United States Patent [19]
Ostroff et al.

[11] Patent Number: 4,595,660
[45] Date of Patent: Jun. 17, 1986

[54] **MOLECULAR CLONING WITH BIFUNCTIONAL PLASMID VECTORS IN *BACILLUS SUBTILIS*, MUTANTS AND SUBSTANTIALLY STABLY TRANSFORMED MUTANTS OF *BACILLUS SUBTILIS*, AND METHODS FOR UTILIZING THE TRANSFORMED MUTANTS**

[75] Inventors: Gary R. Ostroff, Needham, Mass.; Jacques J. Pène, Newark, Del.

[73] Assignee: University of Delaware, Newark, Del.

[21] Appl. No.: 471,789

[22] Filed: Mar. 2, 1983

[51] Int. Cl.$^4$ .................... C12R 1/125; C12N 15/00; C12N 1/20; C12N 1/00; C12P 21/00

[52] U.S. Cl. .................................. 435/172.3; 435/68; 435/253; 435/317; 435/839; 935/27; 935/56; 935/74

[58] Field of Search ...................... 435/68, 869, 172.1, 435/172.3, 172, 253, 317

[56] References Cited

U.S. PATENT DOCUMENTS

| | | | |
|---|---|---|---|
| 4,237,224 | 12/1980 | Cohen et al. | 435/68 |
| 4,302,544 | 11/1981 | Young et al. | 435/253 |
| 4,419,450 | 12/1983 | Dean et al. | 435/172.3 |

FOREIGN PATENT DOCUMENTS

| | | | |
|---|---|---|---|
| 0029497 | 6/1981 | European Pat. Off. | 435/253 |
| 0063494 | 10/1982 | European Pat. Off. | 435/172 |
| 0063953 | 11/1982 | European Pat. Off. | 435/172 |
| 2090600 | 7/1982 | United Kingdom | 435/172 |

OTHER PUBLICATIONS

Tanaka, T., *Mol Gren Genet*, vol. 175, p. 235, 1979.
Gryczan et al, *J of Bact.*, v. 134, No. 1, Apr. 1978, "Characterization of *Staphylococcus aureus* Plasmids Introduced by Transformation into *Bacillus subtilis*".
Gryczan et al, Proc Nat'l Acad Sci, v. 75, No. 3, pp. 1428–1432, Mar. '78, "Construction and Properties of Chimeric Plasmids in *Bacillus subtilis*".
Lovett et al., Chemical Abstracts, v. 94, No. 80124x, 1981, "Molecular Cloning of *Bacillus subtilis* Using Plasmid Vectors".
Gray et al, *J of Bact.*, v. 145, No. 1, pp. 422–428, Jan. 1981, "Molecular Cloning and Expression of *Bacillus licheniformis* β lactamase Gene in *Escherichia coli* and *Bacillus subtilis*".
Keggins et al, *Proc. Nat'l Acad Sci*, v 75, No. 3, pp. 1423–1427, Mar. 1978, "Molecular Cloning of Genetically Active Fragments of Bacillus DNA in *Bacillus subtilis* and Properties of the Vector Plasmid pUB110".
Ehrlichs, *Proc. Nat'l Acad Sci*, v 75, No. 3, pp. 1433–1436, Mar. '78, "DNA Cloning in *Bacillus subtilis*".
Gryczan et al, *J of Bact.*, v. 141, No. 1, Jan. 1980, "Characterization of Chimeric Plasmid Cloning Vehicles in *Bacillus subtilis*".

*Primary Examiner*—Thomas G. Wiseman
*Assistant Examiner*—Robin L. Teskin
*Attorney, Agent, or Firm*—Connolly and Hutz

[57] ABSTRACT

A mutant of *Bacillus subtilis* has been isolated which greatly facilitates gene cloning in this nonpathogenic microorganism. *B. subtilis* is a known protein secretor and can be used efficiently in commercial operations. Unlike the more commonly used clone-propagating organism *E. coli.*, *B. subtilis* has the advantage of lacking pyrogenic substances in its cell envelope. However, chimeric plasmids for infection of *B. subtilis* have been difficult to prepare, and if *E. Coli* is used as an intermediate host to provide plasmid forms suitable for Bacillus transformation, the *B. subtilis* treats any *E. coli*-propagated DNA as foreign and preferentially attacks the insert portion of the plasmid. This attach results in loss of cloned genes and limits the use of *B. subtilis* as a cloning system. The *B. subtilis* recipient strain of this invention is, on the other hand, stably and efficiently transformed by *E. coli*-propagated plasmid DNA at high frequency. The discovery of this mutant and the substantially higher frequency stable transformants obtained from it greatly facilitates the use of *B. subtilis* as a host for the expression of cloned genes.

8 Claims, No Drawings

MOLECULAR CLONING WITH BIFUNCTIONAL PLASMID VECTORS IN BACILLUS SUBTILIS, MUTANTS AND SUBSTANTIALLY STABLY TRANSFORMED MUTANTS OF BACILLUS SUBTILIS, AND METHODS FOR UTILIZING THE TRANSFORMED MUTANTS

The Government has rights in this invention pursuant to research grant number 5 R01 A116132 awarded by the National Institutes of Health.

TECHNICAL FIELD

This invention relates to the substantially stable transformation of *Bacillus subtilis* with a bifunctional chimeric vector, which vector would normally be subject to degradation by the *B. subtilis* host. An aspect of this invention relates to the isolation of a mutant of *B. subtilis* which is capable of substantially stable transformation by clone pools or by individual recombinant bifunctional plasmids propagated in *Escherichia coli*. Another aspect of this invention relates to the transformation of these mutants to obtain substantially stable transformants. Still another aspect of this invention relates to the use of the transformants in biosynthetic methods. Still another aspect of this invention relates to a bifunctional plasmid suitable for use in the method for isolating the mutant of *B. subtilis*.

DESCRIPTION OF THE PRIOR ART

Although recombinant DNA technology is a relative newcomer among the biological and biochemical sciences, this field is already well developed, and scientists have been experimenting for some time with transfer of plasmids among bacteria. Cloning via plasmids (e.g. using enzymes and DNA fragments) is both well-developed and commercially significant. It has been demonstrated that genes derived from totally different biological classes can be replicated in certain host organisms (such as *Escherichia coli*), thereby resulting in the attainment of interspecies genetic expression. A variety of new characteristics or phenotypes have been conferred upon host organisms by rendering these organisms competent and infecting them with the desired chimeric plasmids.

Various strains of *E. coli* have been among the workhorses of recombinant DNA research and development and are still used extensively despite the opening of the field to other species. *E. coli* has a number of important advantages, but its disadvantages are among the factors which have induced researchers to investigate other host organisms. For example, the cell envelope components of *E. coli* include pyrogens. Furthermore, *E. coli* strains do not typically excrete extracellular protein, thereby complicating product recovery when the *E. coli* transformants are used for in vivo biological synthesis in commercial operations.

A potentially attractive alternative to *E. coli* is the soil bacterium *B. subtilis*. This microorganism is nonpathogenic to humans, lacks toxins and toxic cell envelope components, and can be used with great efficiency in commercial fermentation applications. For example, this species of Bacillus is capable of producing extracellular proteins, thereby simplifying recovery when the protein is the desired product. Accordingly, work has recently been directed to attempts to develop *B. subtilis* as a cloning system, so that transformants of this species can be used to produce extracellular proteins not obtainable from the naturally-occurring soil bacterium having the naturally-occurring genetic background. In addition, *B. subtilis* has a well-characterized genetic map, a DNA-mediated transformation system, and several lysogenic and virulent bacteriophages with potential applications as cloning vehicles.

Although several plasmids originally isolated in *Staphylococcus aureus* can propagate in *B. subtilis*, direct cloning of DNA sequences with these vehicles is very inefficient when compared with the *E. coli* system. The problem, in part, is that *B. subtilis* requires plasmic multimers (e.g. dimers, trimers, etc.) for efficient transformation of competent recipient cells. For this reason, most *B. subtilis* sequences have been cloned directly in *E. coli* where transformation is straightforward. To overcome the requirement for plasmid multimers, Rappaport et al, in Mol. Gen. Genet. 176:239 (1979) first cloned *B. subtilis* DNA with a bifunctional vector in *E. coli*. The objective in this case was to generate chimeric plasmid multimers in *E. coli* and then use these multimers to transform competent *B. subtilis* recipients. Unfortunately, the present indications are that the transformants obtained in this manner are unstable. Upon transfer or within a few generations, the transformants lose, so to speak, their newly acquired characteristics. (In the context of this application, such loss of new characteristics is referred to as "instability", and transformants which breed true and retain their newly acquired characteristics through an apparently indefinite number of generations are referred to as "stable" transformants.)

It may be assumed that, if the intermediate host could be avoided, stable *B. subtilis* transformants could be obtained. However, the typical recombinant plasmids produced in vitro are monomeric; that is, they contain only one complete genetic unit. Such monomers will not be transferred to and propagated in *B. subtilis* at any practical frequency. ("Frequency" is defined as the number of positive events divided by the number of total events which occurred.) The use of the intermediate host, on the other hand, is an attractive way to develop a substantial population of multimeric plasmids. Theoretically, it should be possible to provide a chimeric monomeric bifunctional shuttle vector in vitro, transfer this vector to *E. coli*, obtain a population of multimers, and infect the *B. subtilis* with the multimeric plasmids. The reasons for the principal difficulty connected with this strategy—i.e. the apparent instability of the *B. subtilis* transformants and poor transformation frequency—are not fully understood.

This invention contemplates a solution to the unstable transformation problem encountered when bifunctional chimeric plasmids infect *B. subtilis*.

The following references are considered representative of the state of this art:

Ehrlich, Proc. Natl. Acad. Sci., 75, 1433–1436 (1978), Gryczan, et al., J. Bacteriol. 134, 318–323 (1978), Keggins, et al., Proc. Natl. Acad. Sci 75, 1423–1427 (1978), Kawamura, Gene 5, 87–91 (1979), Gryczan, et al., J. Bacteriol. 141, 246–253 (1980), Rappaport, et al., Mol. Gen. Genet 176, 239–245 (1979), Tanaka, et al., Gene 10, 131–136 (1980) and Ferrari et al., J. Bacteriol 152, 809–814 (1982). See also Gray and Chang, J. Bacteriol. 145, 422 (1981).

U.S. Pat. No. 4,237,224 (Cohen and Boyer), issued Dec. 2, 1980, discloses procedures useful in the present invention. Other literature cited in this specification relating to procedures employed is to be considered incorporated by reference.

SUMMARY OF THE INVENTION

Although this invention is not bound by any theory, our most important theoretical findings suggest the reasons why the *B. subtilis* transformation strategy of this invention appears to produce substantially stable transformants.

Among these theoretical findings are the following. First, the cloned inserts are unstable after the multimeric plasmid has been transferred from the intermediate *E. coli* host to the *B. subtilis*. After a relatively short period of time and within a few generations, the inserts are severely damaged, e.g. by deletions. Second, the extent of the damage seems to depend on (1) the genetic background of the *B. subtilis* recipients and (2) the size of the cloned inserts. The frequency of chimeric plasmid deletions appears to be increased in restriction-proficient recipients; however, in the restriction-deficient strain MI 112, deletions were nevertheless observed, and their frequency was proportional to insert size. Third, even in the strain MI 112, the damage appeared to be restriction-mediated. Fourth, studies with radioactive phosphorous-labeled plasmids suggest that at least some of the damage to the inserts is endonucleolytic and extracellular. Fifth, in the course of studying a very large number of MI 112 transformants for intact chimeric plasmid DNA, the chimeric plasmid DNA having been propagated in *E. coli* prior to the transformation of the *B. subtilis* recipients, occasional occurrences of intact inserts were found. Sixth, plasmid instability appears to result from propagation through *E. coli;* chimeras propagated in *B. subtilis* are far more effective in providing stable transformation of *B. subtilis* recipients than are those propagated through *E. coli*.

With these findings as background, a highly transformable mutant of *B. subtilis* (hereinafter referred to as "PSL1")has been found. This mutant differs phenotypically from the parent strain as shown by (1) stable transformation by individual recombinant bifunctional plasmids from *E. coli*, (2) increased stable transfer of certain clone pools from *E. coli*, and (3) an apparently reduced tendency toward endonucleolytic degradation of extracellular heterologously propagated chimeric plasmid DNA.

This mutant can be substantially stably transformed by any of a variety of suitable recombinant bifunctional plasmids propagated in *E. coli*. As a result, novel transformants with practical utility as extracellular protein secretors can be obtained from the *B. subtilis* mutant, thereby making possible a vast expansion of *B. subtilis* biosynthesis technology.

The mutant was isolated by:

(a) propagating a recombinant bifunctional plasmid in *E. coli*, (b) transforming a restriction-deficient strain of *B. subtilis* with the thus-propagated chimeric plasmid to obtain a population of *B. subtilis* transformants most of which were unstable, (c) isolating the very few substantially stable transformants, (d) curing the substantially stable transformants by growing them for several generations without selective pressure from an antibiotic, and (e) detecting and selecting the mutant from among the cured later generations, preferably by stable retransformation with the original recombinant plasmids which were initially unstable.

Regarding MI 112, the preferred restriction-deficient parent strain, see T. Tanaka, Mol. Gen. Genet. 175:235 (1979). The ATCC number for this strain is 33712.

Colonies of the cured mutant can be grown in large numbers, and these mutants can be substantially stably transformed with recombinant bifunctional plasmids propagated in *E. coli.*

Because of the apparently significant relationship between the size of the insert and the extent of damage targeted toward cloned inserts, even when the damage is done by restriction-deficient strains of *B. subtilis,* a recombinant plasmid was constructed for the mutant isolation method of this invention, which plasmid contains a cloned insert of *B. subtilis* DNA having a readily determinable or detectible length (or molecular weight) useful in the method. Although this stretch of DNA may be as small as two hundred or three hundred base pairs or as large as 20,000 base pairs (20 Kbp), relatively longer stretches of DNA (>4 Kbp) are much more likely to be damaged, thereby reducing the efficiency of this mutant isolation method. The cloned insert can be detected in its intact form by known molecular weight determination techniques.

Organism Culture Deposit

The highly transformable *B. subtilis* mutant of this invention ("PSL1") has been grown in suitable media, and a culture was deposited on Feb. 25, 1983 with the Bacillus Genetic Stock Center (Ohio State University Department of Microbiology, Columbus, Ohio, U.S.A.) under culture number BGSC 1A510.

The above-identified "PSL1" mutant is also deposited with the American Type Culture Collection (A.T.C.C.) under A.T.C.C. accession number 39620.

DETAILED DESCRIPTION

The development of the method for isolating the mutant referred to hereinafter as *B. subtilis* PSL1 or simply PSL1(a mutant of the MI 112 strain) made use of materials readily available to those skilled in the field of recombinant DNA technology, and many of the method steps have been described in the literature. Various strains of *B. subtilis* and *E. coli* are, of course, available to skilled researchers. These strains can be grown in readily available media, including media provided with antibiotics in order to test the efficiency of transformation. A variety of plasmids, including bifunctional cloning vectors have been described in the literature, and their construction has become relatively straightforward.

A typical *B. subtilis* strain useful in this invention, MI 112 has been mentioned previously. Its relevant genotype is leuA8 arg15 thrA recE4 r$^-$m$^-$. Typical *E. coli* strains include SK2267 and C600 SF8. As noted previously, *E. coli* was the intermediate host used to propagate monomeric plasmids to obtain populations containing useful amounts of various multimers (dimers, trimers, tetramers, etc.). Bifunctional plasmid vectors capable of infecting both the intermediate host *E. coli* and *B. subtilis* have been described in the literature, e.g. Rappaport et al., Mol. Gen. Genet. 176:239-245 (1979) and Gray and Chang, J. Bacteriol. 145:422-428 (1981).

These and other materials and methods used in this invention will now be described in greater detail.

The Plasmid Vector

As is known in the art, monomeric bifunctional cloning vectors can be constructed in vitro from supercoiled plasmids which are provided with inserts using nucleases and ligases. The size of inserts is an important consideration in this invention, as is the ease of infecting the intermediate *E. coli* host and the desired *B. subtilis* strain. The bifunctional plasmid vector can be provided with phenotypic properties, e.g. antibiotic resistance, which is expressed in the intermediate host and in *B. subtilis*. Antibiotic resistance is a particularly useful property, since it facilitates the selection and isolation steps used in methods of this invention. Bifunctional vectors reported in the literature will confer a resistance to a first antibiotic (e.g. ampicillin, tetracycline, etc.) in the *E. coli* transformant and usually a second, different antibiotic resistance (e.g. to chloramphenicol or to kanamycin) in the *B. subtilis* transformant. There may be more than one antibiotic resistant property conferred (e.g. both ampicillin and tetracycline resistance in *E. coli*) as a result of a transformation.

Although plasmids have been found in naturally-occurring *B. subtilis* organisms, these naturally occurring plasmids have not been useful, since they do not encode antibiotic resistance determinants and have therefore no selectable phenotype. But plasmids from other gram-positive microorganisms (believed by some researchers to be close in evolution to the genus Bacillus) can be used or adapted for replication in *B. subtilis*. As noted previously, plasmids originally isolated in *S. aureus* will be taken up by competent *B. subtilis* cells, although infectivity requires plasmid multimers. (*B. subtilis* cells can be grown such that they will be "naturally" competent, i.e. capable of taking up the plasmids.)

Of the known bifunctional vectors, several are suitable for use in this invention which have been disclosed in the literature, e.g. Rappaport et al, Mol. Gen. Genet. 176:239 (1979). A series of vectors has been reported by Goebel et al, in Boyer et al (Ed.), Genetic Engineering, Elseveer, N. Holland, Amsterdam, 1978, pp. 47–58. Another bifunctional vector (subsequently referred to as "pDH5060") has been constructed by Gray and Chang by linking pOG1196 (a chimera of pC194 and pUB110) to pBR322 at their unique Pvu II sites. This plasmid (pDH5060) replicates in both *E. coli* and *B. subtilis* and confers a first antibiotic resistance (to both ampicillin and tetracycline) in *E. coli* and a second antibiotic resistance (to chloramphenicol) in *B. subtilis*. This vector which has been described in the literature contains unique Bam Hl and Sal I sites within the Tc gene, thus allowing identification of recombinant molecules by insertional inactivation. See Gray and Chang, J. Bacteriol. 145:422–428 (1981).

Another vector (hereinafter referred to as "pLP1201") was derived from pDH5060 by retaining the HindIII site within the pBR322 sequences of the plasmid, and deleting the other HindIII site located near the chloramphenicol-resistance determinant of the pC194 contribution. pDH5060 CCC (covalently closed circular) DNA was linearized with low concentrations of HindIII (0.1 unit/μg; 37° C., 1 hour) to cleave the plasmid at either site, ethanol precipitated and resuspended in high salt buffer (280 mM NaCl, 30 mM sodium acetate, 4.5 mM zinc acetate). The DNA was then treated with S1 nuclease (1 unit/μg) at 37° C. for 30 minutes to blunt the exposed HindIII termini. After addition of EDTA to a final concentration of 10 mM, the DNA was heated for 10 min. at 65° C. and electrophoresed on a 1% agarose gel. Linear molecules with a 7500 base pair (7.5 Kbp) sequence were recovered from the gel by freeze-thawing, phenol extracted twice and concentrated by ethanol precipitation from 1M ammonium acetate.

After blunt end ligation with T4 DNA ligase (50 units/ml, 14° C., 18 hours), the DNA was transformed into *E. coli* C600SF8, scoring for ampicillin-resistant transformants. Since the two HindIII of pDH5060 are separated by about 2.4 Kilo-base pairs (Kbp), and since this stretch of DNA is cleaved asymmetrically by Bam Hl, it was ascertained which of the two HindIII sites had been deleted from individual ampicillin-resistant transformants by Bam Hl-HindIII double digestion. The desired plasmid, pLP1201, generated 7.1 and 0.4 Kbp fragments indicating that the HindIII site within the pBR322 contribution had been retained.

With a unique HindIII site near the promoter for the tetracycline resistance determinant, pLP1201 was used to clone purified bacteriophage φ29 HindIII fragments.

Isolation of Plasmid DNA and Preparation of Competent Cells

CCC-plasmid DNA was purified from stationary phase *E. coli* cultures essentially by the cleared-lysate cesium chloride ethidium bromide method described by Kupersztoch and Helsinki, Biochem. Biophys. Res. Comm. 54:1451–1459 (1973) and Radloff et al, Proc. Natl. Acad. Sci. USA 57:1514–1521 (1967).

Plasmid DNA was purified from cultures of *B. subtilis* grown overnight at 37° C. in a medium containing chloramphenicol as described above for *E. coli*.

Plasmid transformation of *E. coli* SK2267 was carried out using competent cells prepared according to the known $CaCl_2$ method. Resistant cells were selected on agar plates containing ampicillin or tetracycline. Competent *B. subtilis* cells were prepared essentially as described by Contente and Dubnau, Mol. Gen. Genet. 167:251–258 (1979). Optimal conditions for plasmid transformation were empirically determined for the preferred *B. subtilis* strain. Selection for chloramphenicol resistance was carried out on agar plates containing chloramphenicol following incubation of competent cells and DNA for 1 hour at 37° C.

A variety of plasmids and chimeric plasmids can be derived from pDH5060 to provide inserts ranging in size from about 0.3 Kbp to about 20 Kbp. For the isolation method described subsequently, the size range selected was about 1.7 Kbp to 9.5 Kbp.

Isolation of the *B. Subtilis* Mutant With Improved Transformability With Respect to Plasmids Propagated in *E. Coli*

*B. subtilis* transformants were obtained from the MI 112 strain with plasmid vectors as described previously. See the method of Rappaport et al., Mol. Gen. Genet. 176:239 (1979).

Based upon the theoretical findings described previously, it was suspected that occurrence of rare, stable chloramphenicol-resistant transformants could result from either chance events or from phenotypic changes in the recipient. Five hundred MI 112 transformants were examined to detect intact chimeric plasmid DNA. Twenty MI 112 chloramphenicol-resistant transformants containing intact plasmid or hybrid plasmid DNA were chosen. These stable transformants were spontaneously cured of plasmid DNA (grown out for 20 generations without chloramphenicol). (*B. subtilis* strains spontaneously lose pDH5060 chimeras when cells are grown in the absence of chloramphenicol selection at a rate of about 10% per generation.) The cured colonies were confirmed to be plasmid-free. Cured derived strains were then made competent and retransformed with suitable plasmids or chimeric plasmids (e.g. pDH5060). Retransformation frequencies of cured strains by chimeric plasmid DNA ranged up to 100-fold higher than the parental strain MI 112. Five of the cured strains were retransformed to reacquire chloramphenicol resistance at an increased frequency by three different chimeric plasmids. However, only one cured strain, previously designated herein as PSL1, was stably retransformed by plasmid chimeras.

Characterization of the Transformation Phenotype of PSL1

The chimeric plasmid transformation efficiency of PSL1 was compared to the parent strain MI 112 with native pDH5060, pDH5060 homologous and pLP1201 heterologous chimeras propagated in *E. coli*. PSL1 and MI 112 (the parent strain) were transformed at similar efficiency with the vector pDH5060. However, chimeras isolated from *E. coli* transformed PSL1 5 to 110-fold higher than parental strain MI 112. The greatest improvement in transformation efficiency was observed with chimeras containing inserts of 4 Kbp and smaller; hybrid plasmids containing large inserts (>5 Kbp) transform strain MI 112 poorly.

The phenotype of strain PSL1 also resulted in increased short-term stability of chimeric plasmid DNA transferred from *E. coli*. This increase in stability was up to 100% for plasmids containing inserts 1.7–4.2 Kbp in length, but was reduced to 25% for the transfer of the large chimera containing a *B. subtilis* 9.5 Kbp insert. Thus, PSL1 is a highly transformable recE4 strain of *B. subtilis* which allows stable transfer of individual recombinant plasmid DNA molecules containing inserts up to at least 4 Kbp in length from *E. coli* to *B. subtilis*.

In the method of this invention, plasmid DNA uptake and formation of extracellular and intracellular acid-soluble material were determined essentially by the method of de Vos et al., Mol. Gen. Genet. 181:424–433 (1981). Both the parent *B. subtilis* strain MI 112 and the mutant PSL1 were investigated regarding extracellular and intracellular stability and kinetics of DNA uptake of $^{32}$P-labeled *E. coli*- and *B. subtilis*-propagated chimeric plasmid DNAs. Characterization of $^{32}$P-labeled chimeric plasmid DNA during transformation of PSL1 and the parental strain MI 112 revealed no differences in plasmid DNA uptake or extracellular and intracellular acid-soluble radioactivity. However, extracellular *E. coli*-propagated chimeric plasmid DNA was substantially endonucleolytically degraded after 30–60 minutes incubation with strain MI 112 but not PSL1.

Transfer of *B. Subtilis* Clone Banks From *E. Coli* to PSL1

To determine if the transformable phenotype of PSL1 extended to the transfer of pDH5060 clone banks between *E. coli* and MI 112, clone pools of *B. subtilis* sequences propagated in *E. coli* were used to transform MI 112 and PSL1. Clone pools of pDH5060 chimeras propagated in *E. coli* transform MI 112 at low efficiency (0.1–1% of the transformation by native pDH5060 vector), but it was found that PSL1 was transformed at high efficiency, ranging from 20 to 100-fold higher than MI 112. The effect of the mutation in PSL1 on the stable transfer of two *B. subtilis* clone pools from *E. coli* to *B. subtilis*, and between *E. coli* strains was investigated. To determine the physical integrity of transferred *E. coli* propagated chimeras, $10^3$ to $10^4$ transformants were pooled and plasmid DNA isolated and analyzed by agarose gel electrophoresis after restriction nuclease digestion. As a control, the recovery of individual recombinant plasmids in clone pools transferred between *E. coli* strains SK2267 and C600SF8 was examined and found to average 80%. In contrast, stable transfer of individual recombinant plasmids in these clone pools to MI 112 was very inefficient, averaging 13%. However, transfer of hybrid plasmids in these clone pools from *E. coli* to PSL1 resulted in an increased recovery of individual stable chimeras (up to 50%) from pooled chloramphenicol-resistant transformants. Thus the phenotype of PSL1 allows the stable transfer of both individual chimeras and clone pools from *E. coli* to *B. subtilis* at an increased efficiency.

Although this invention is not bound by any theory, it is believed that the basis for unstable, inefficient transformation of *B. subtilis* MI 112 with suitable recombinant plasmids from *E. coli* lies in targeting of cloned genes for deletion by an enzyme or enzymes of MI 112, despite the restriction-deficient character of this strain. It is believed that the enzyme(s) recognize *E. coli*-propagated DNA molecules as foreign. This results in a serious loss of cloned genes, severely limiting the use of MI 112 and other commonly-used *B. subtilis* strains as a cloning system. The mutant PSL1, on the other hand, propagates cloned genes in Bacillus in a stable manner. This discovery can largely overcome a serious obstacle to the use of *B. subtilis* as a host bacterium for the expression of cloned genes.

What is claimed is:

1. A biologically pure culture of a spontaneous mutant of the MI 112 strain of *Bacillus subtilis*, said mutant being identified by the Bacillus Genetic Stock Center culture number BGSC 1A510.

2. A culture according to claim 12 in which the mutant has been substantially stably transformed by a recombinant bifunctional plasmid propagated in *Escherichia coli*.

3. A culture according to claim 2 in which the substantially stably transformed mutant is capable of producing a protein which is not produced by said MI 112 strain, as a result of the transformation by said recombinant bifunctional plasmid.

4. A culture according to claim 2 in which the substantially stably transformed mutant has resistance to an antibiotic as a result of the transformation.

5. A method for isolating the spontaneous mutant of the MI 112 strain of *Bacillus subtilus* identified by the Bacillus Genetic Stock Center culture number BG SC 1A510 comprising the following steps:
   a. propagating a recombinant or chimeric bifunctional plasmid in *Eschericia coli*, said plasmid including a first DNA region capable of conferring a first antibiotic resistance in *Eschericia coli*, a second DNA region capable of conferring a second antibiotic resistance in *Bacillus subtilis*, and a third DNA region comprising a cloned insert;
   b. transforming the *Bacillus subtilis* strain with the thus-propagated plasmid to obtain a population of *Bacillus subtilis* MI 112 transformants comprising a major amount of second antibiotic-resistant, unstable transformants and a minor amount of second antibiotic-resistant, substantially stable transformants containing the said third DNA region intact, said minor amount of substantially stable transformants including a spontaneous mutant;

c. separating the minor amount of substantially stable transformants from said major amount of unstable transformants;

d. curing the substantially stable transformants of the antibiotic-resistant characteristic by growing a multiplicity of generations of said transformants without selective pressure from an antibiotic, thereby permitting later generations of said transformants to lose said characteristic;

e. selecting the spontaneous mutant from among the cured later generations.

6. A method according to claim 5, wherein, in step (e), the spontaneous mutant is selected by retransformation of said cured later generations with a recombinant or chimeric plasmid containing said third DNA region and then determining the stability of the third DNA region in the cured later generations.

7. A method for transforming the spontaneous mutant of the MI 112 strain of *Bacillus subtilis* identified by the Bacillus Genetic Stock Center culture number BGSC 1A510 comprising the following steps:

a. conducting the infection of said mutant with a multimeric plasmid propagated in *Escherichia coli* in a medium under conditions to form a transformant colony of said mutant, said multimeric plasmid being capable of conferring phenotypical resistance to an antibiotic, thereby conferring resistance to said antibiotic upon the transformant colony;

b. separating the transformant colony from the medium;

c. transferring the transformant colony to a medium containing said antibiotic; and d. recovering transformant organisms surviving said antibiotic.

8. A method for producing a producing a protein foreign to *Bacillus substilus* which comprises;

transforming a spontaneous mutant of the MI 112 strain of *Bacillus subtilus*, said mutant being identified by the Bacillus Genetic Stock Center Culture Number BGSC 1A510, with a recombinant plasmid comprising a gene encoding for said protein;

culturing said transformed mutant under conditions suitable for the expression of said gene; and isolating the expressed protein from the culture.

* * * * *